(12) United States Patent
Zhang

(10) Patent No.: US 8,240,219 B2
(45) Date of Patent: Aug. 14, 2012

(54) APPARATUS FOR TESTING OBJECT STRENGTH

(75) Inventor: Bing-Jun Zhang, Shenzhen (CN)

(73) Assignees: Hong Fu Jin Precision Industry (ShenZhen) Co., Ltd., Shenzhen, Guangdong Province (CN); Hon Hai Precision Industry Co., Ltd., Tu-Cheng, New Taipei (TW)

( * ) Notice: Subject to any disclaimer, the term of this patent is extended or adjusted under 35 U.S.C. 154(b) by 352 days.

(21) Appl. No.: 12/635,667

(22) Filed: Dec. 10, 2009

(65) Prior Publication Data

US 2010/0307260 A1    Dec. 9, 2010

(30) Foreign Application Priority Data

Jun. 5, 2009   (CN) .......................... 2009 1 0302956

(51) Int. Cl.
*G01N 3/00*   (2006.01)

(52) U.S. Cl. ........................................................ 73/838

(58) Field of Classification Search .................... 73/838
See application file for complete search history.

(56) References Cited

U.S. PATENT DOCUMENTS 5,111,701 A * 5/1992 Klein ............................... 73/827
5,906,538 A * 5/1999 Welch ........................... 451/241

FOREIGN PATENT DOCUMENTS

CN         2856976 Y    1/2007
CN       201218763 Y    4/2009

\* cited by examiner

*Primary Examiner* — Lisa Caputo
*Assistant Examiner* — Octavia D Davis-Hollington
(74) *Attorney, Agent, or Firm* — Altis Law Group, Inc.

(57) ABSTRACT

An apparatus for testing strength of a corner portion of an object includes a support platform, an installation mechanism having a slidable plate mounted on the platform, a force gauge fixed to the slidable plate, a drive mechanism connected to the slidable plate to move the slidable plate, and a push-pull mechanism. The push-pull mechanism is connected to the force gauge to be pushed or pulled by the force gauge and exerts push or pull force on the corner portion of the object.

14 Claims, 5 Drawing Sheets

APPARATUS FOR TESTING OBJECT STRENGTH

CROSS-REFERENCES TO RELATED APPLICATION

A relevant subject matter is disclosed in the co-pending U.S. patent application Ser. No. 12/551,444 filed on Aug. 31, 2009, and entitled "APPARATUS FOR TESTING STRENGTH OF OBJECTS", and a co-pending U.S. patent application entitled "APPARATUS FOR TESTING OBJECT STRENGTH" filed at the same date as this patent application, which are assigned to the same assignee as this patent application.

BACKGROUND

1. Technical Field

The disclosure relates to apparatuses for testing object strength, and particularly, to an apparatus for testing strength of molded products.

2. Description of Related Art

Typically, corners of an injection molded product are formed by influx of two or more streams of molten material. As a result, the corners may not bind well, presenting relative weakness of the seal therebetween. Consequently, a risk of rupture is present.

In practice, there is a need to test the strength of injection molded products at corners. Typically, the sides near the corners of the products are pulled manually to test the rupture strength. However, the manual test is not accurate and inefficient.

DETAILED DESCRIPTION

Figure 1:
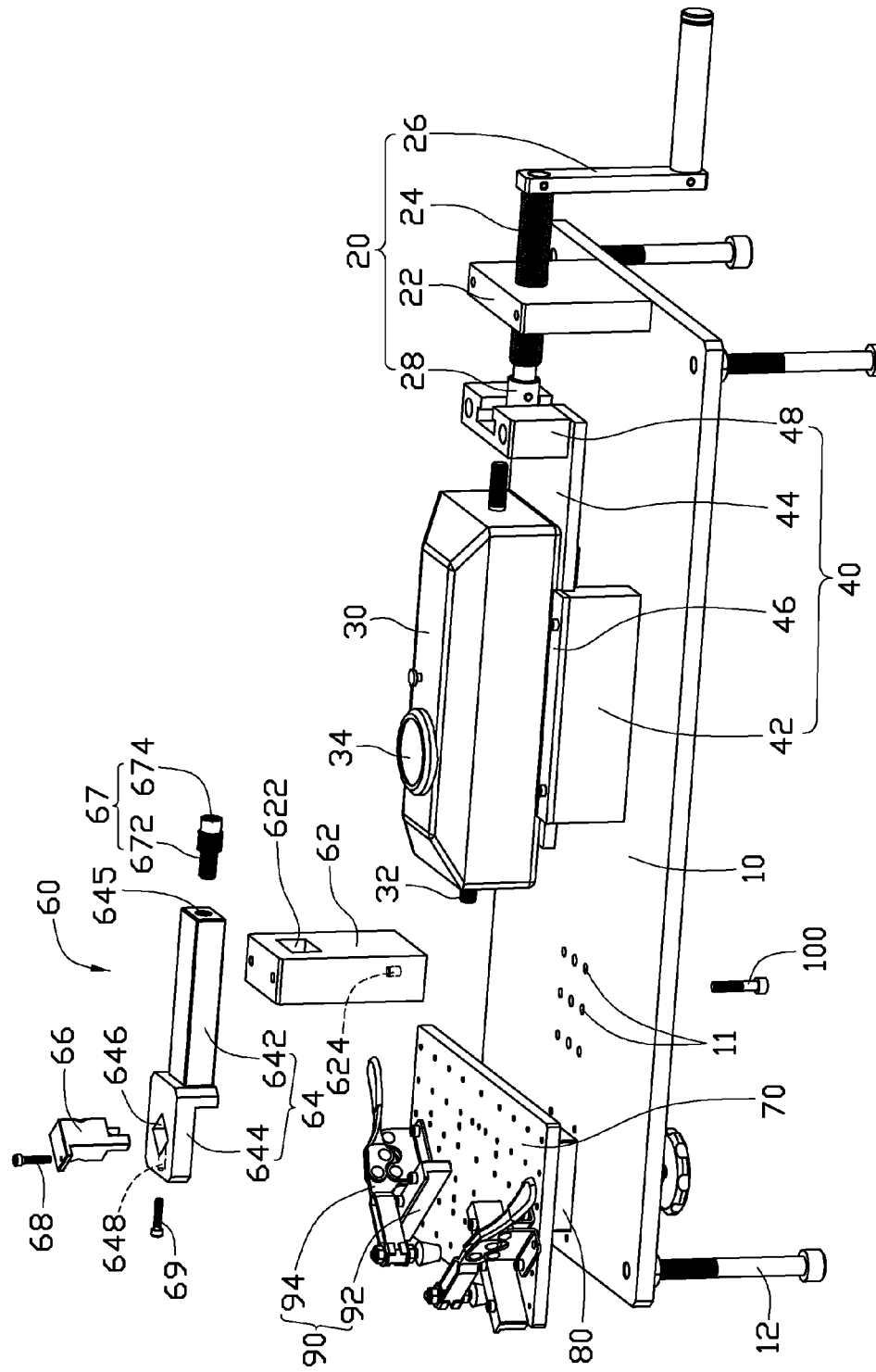
FIG. 1 is an exploded, isometric view showing an exemplary embodiment of an apparatus for testing object strength.

Referring to FIG. 1, a first exemplary embodiment of an apparatus for testing object strength includes a rectangular support platform 10, a plurality of support bolts 12 under the platform 10, an adjustment mechanism 80 installed on a first end of the platform 10, an installation board 70 fixed on the adjustment mechanism 80 for supporting the object, a clamping mechanism 90 which can be placed at different positions on the installation board 70, a drive mechanism 20 installed on a second end of the platform 10 opposite to the first end, a force gauge 30, an installation mechanism 40 positioned between the adjustment mechanism 80 and the drive mechanism 20 for installation of the force gauge 30 thereon, and a push-pull mechanism 60.

The platform 10 includes several sets of installation holes 11 defined therein and between the adjustment mechanism 80 and the installation mechanism 40.

The adjustment mechanism 80 is movable vertical to the platform 10 to adjust the installation board 70.

The clamping mechanism 90 includes two blocking portions 92 and two clamps 94, all of which are installed on the top of the installation board 70.

The drive mechanism 20 includes a support plate 22 extending upright from the second end of the platform 10, a threaded shaft 24 extending through the support plate 22, an L-shaped handle 26 mounted to one end of the threaded shaft 24, and a guide sleeve 28 secured to the other end of the threaded shaft 24.

The force gauge 30 includes two threaded fasteners 32 extending from two opposite end walls thereof, and a dial 34 on a sidewall thereof.

The installation mechanism 40 includes two rail plates 42 extending oppositely from the platform 10, a slidable plate 44 slidably mounted between the rail plates 42 and mounting the force gauge 30, two restricting bars 46 mounted to the tops of the rail plates 42 to restrict two opposite sides of the slidable plate 44, and a drive block 48 mounted on the slidable plate 44 adjacent to the drive mechanism 20. The guide sleeve 28 of the drive mechanism 20 is mounted to the drive block 48 and slidable perpendicular to the platform 10.

The push-pull mechanism 60 includes a stand portion 62, a sliding portion 64 slidably extending through the stand portion 62, a driving portion 66 adjustably mounted to one end of the sliding portion 64, a connecting portion 67, an adjusting element 68 for adjusting the driving portion 66, and a fastener 69. In this embodiment, the adjusting element 68 is a fastener. A rectangular sliding channel 622 is defined through the top of the stand portion 62 parallel to the platform 10. A mounting hole 624 is defined in the bottom of the stand portion 62. The sliding portion 64 includes a rectangular sliding shaft 642 slidably extending through the sliding channel 622, and a mounting section 644 extending from an end of the sliding shaft 642. A securing hole 645 is defined in the other end of the sliding portion 64. A rectangular through hole 646 is defined through the mounting section 644 from top to bottom. A fastener hole 648 is defined in the distal end of the mounting section 644 and communicates with the through hole 646. The through hole 646 is so arranged that one of the four corners is adjacent to the distal end of the mounting section 644, and two sidewalls at the one corner slantingly extend away from the distal end.

Figure 2:
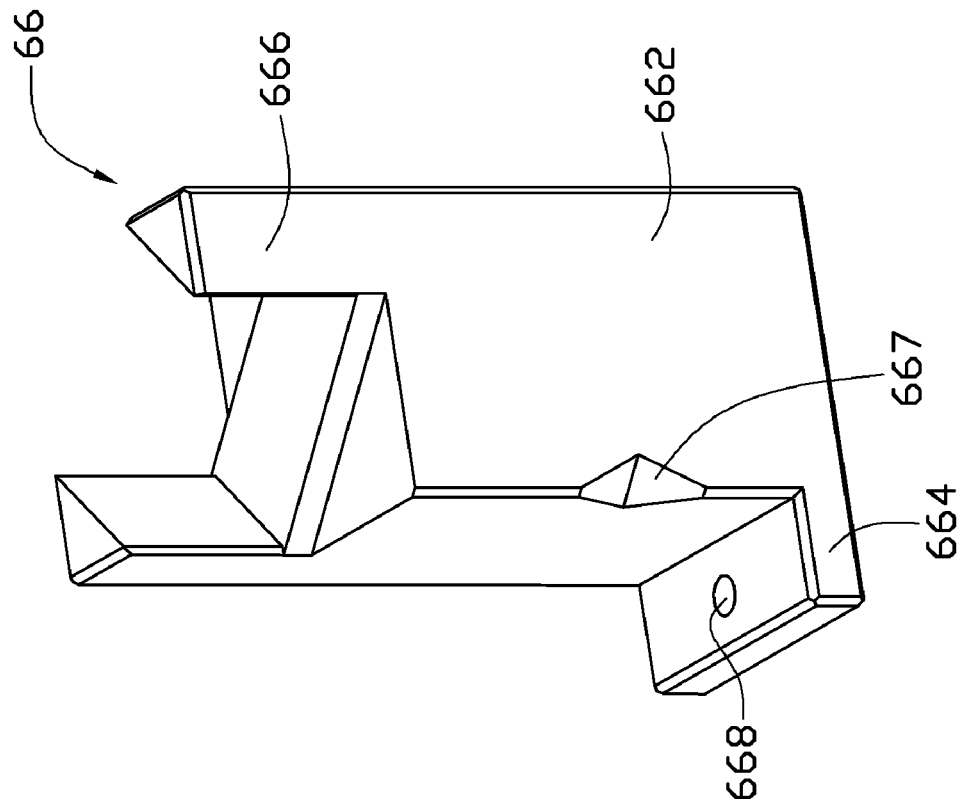
FIG. 2 is an enlarged, isometric view of a driving portion of the apparatus of FIG. 1.

Referring also to FIG. 2 which is an upside down enlarged view of the driving portion 66, the driving portion 66 includes a rectangular main body 662 extending through the through hole 646 of the mounting section 644, a fixing flange 664 extending out from the top of the main body 662, and a pair of forcing posts 666 extending down from two diagonal corners of the bottom of the main body 662. The cross-section of each forcing post 666 is triangular, and two sidewalls of each triangular forcing post 666 are coplanar with two sidewalls of the corresponding corner, respectively. A notch 667 is defined in each of another two diagonal corners of the main body 662. A fixing hole 668 is defined through the fixing flange 664. The connecting portion 67 includes a threaded post 672 at one end corresponding to the securing hole 645 of the sliding portion 64, and a threaded sleeve 674 at the other end corresponding to the threaded fastener 32 of the force gauge 30.

Figure 3:
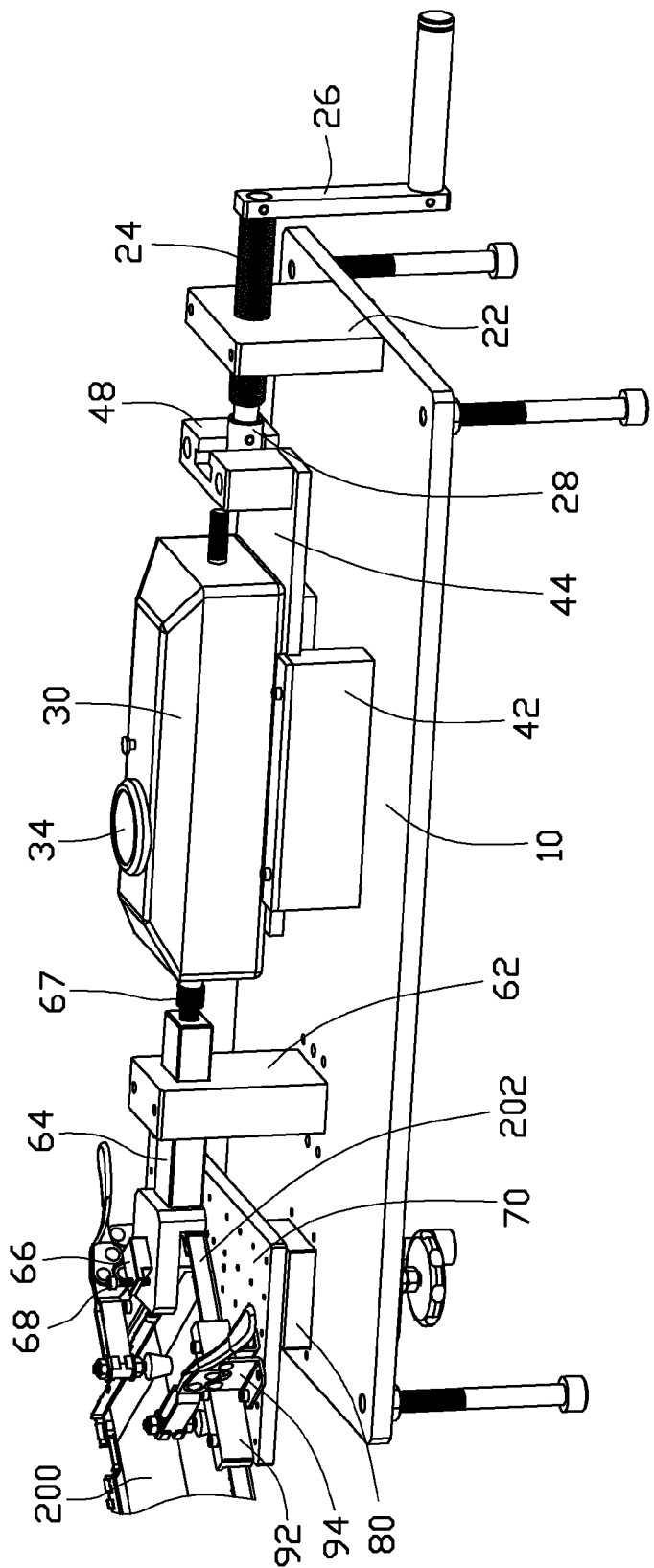
FIG. 3 is an assembled view of the apparatus of FIG. 1, during object testing.

Referring also to FIG. 3, in assembly, a fastener 100 extends through one of the installation holes 11 of the platform 10 and engages in the mounting hole 624 of the stand portion 62 of the push-pull mechanism 60, thereby mounting the stand portion 62 to the platform 10. The threaded post 672 of the connecting portion 67 is threaded in the securing hole 645 of the sliding portion 64. The driving portion 66 of the push-pull mechanism 60 extends through the through hole 646 of the sliding portion 64. The adjusting element 68 is engaged in the fixing hole 668 of the driving portion 66, and the fastener 69 is engaged in the fastener hole 648 of the sliding portion 64. The distal end of the adjusting element 68 abuts the top of the mounting section 644, and the distal end of the fastener 69 abuts the notch 667 of the driving portion 66. The sliding shaft 642 slidably extends through the sliding channel 622 of the stand portion 62. Connecting portion 67 rotates to partly extend the threaded post 672 to engage the threaded sleeve 674 with the threaded fastener 32 of the force gauge 30, which is, accordingly, connected to the sliding portion 64.

In this embodiment, the object to be tested is an injection molded product 200 with a right-angle corner portion 202. During testing, the clamping mechanism 90 is fixed to the installation board 70 according to need, with outer surfaces of two adjacent sides at the corner portion 202 abutting the blocking portions 92, and the clamps 94 clamping the product 200 onto the installation board 70. The adjusting element 68 and the fastener 69 are loosened to abut the sidewalls of the forcing posts 666 against inner surfaces of the two adjacent sides at the corner portion 202. The adjusting element 68 and fastener 69 are tightened, with the distal end of the adjusting element 68 abutting the sliding portion 64, and the distal end of the fastener 69 engaged in the notch 667 of the driving portion 66. Thus, the driving portion 66 is securely mounted to the sliding portion 64.

The handle 26 of the drive mechanism 20 rotates the threaded shaft 24 relative to the support plate 22 and away from the product 200. The slidable plate 44 is moved with the threaded shaft 24 via the drive block 48 and the guide sleeve 28. The force gauge 30 pulls the sliding portion 64 via the connecting portion 67. Therefore, the forcing posts 666 exert pulling force on the inner surfaces of the two adjacent sides at the corner portion 202, causing the two adjacent sides to be deformed toward different directions. When the reading on the dial 34 of the force gauge 30 equals or exceeds a predetermined value, the handle 26 stops rotating. In this circumstance, if the corner portion 202 does not rupture, the strength testing of the product 200 passes; if the corner portion 202 ruptures, the strength testing of the product 200 does not pass. Thus, the testing efficiency is improved, and the labor intensity of the operator is eased.

In other embodiments, the installation board 70 and the adjustment mechanism 80 can be omitted if the blocking portions 92 and clamps 94 are directly mounted onto the first end of the platform 10. In other testing, the apparatus can exert pushing force on the product 202 by reverse rotation of the handle 26.

Figure 4:
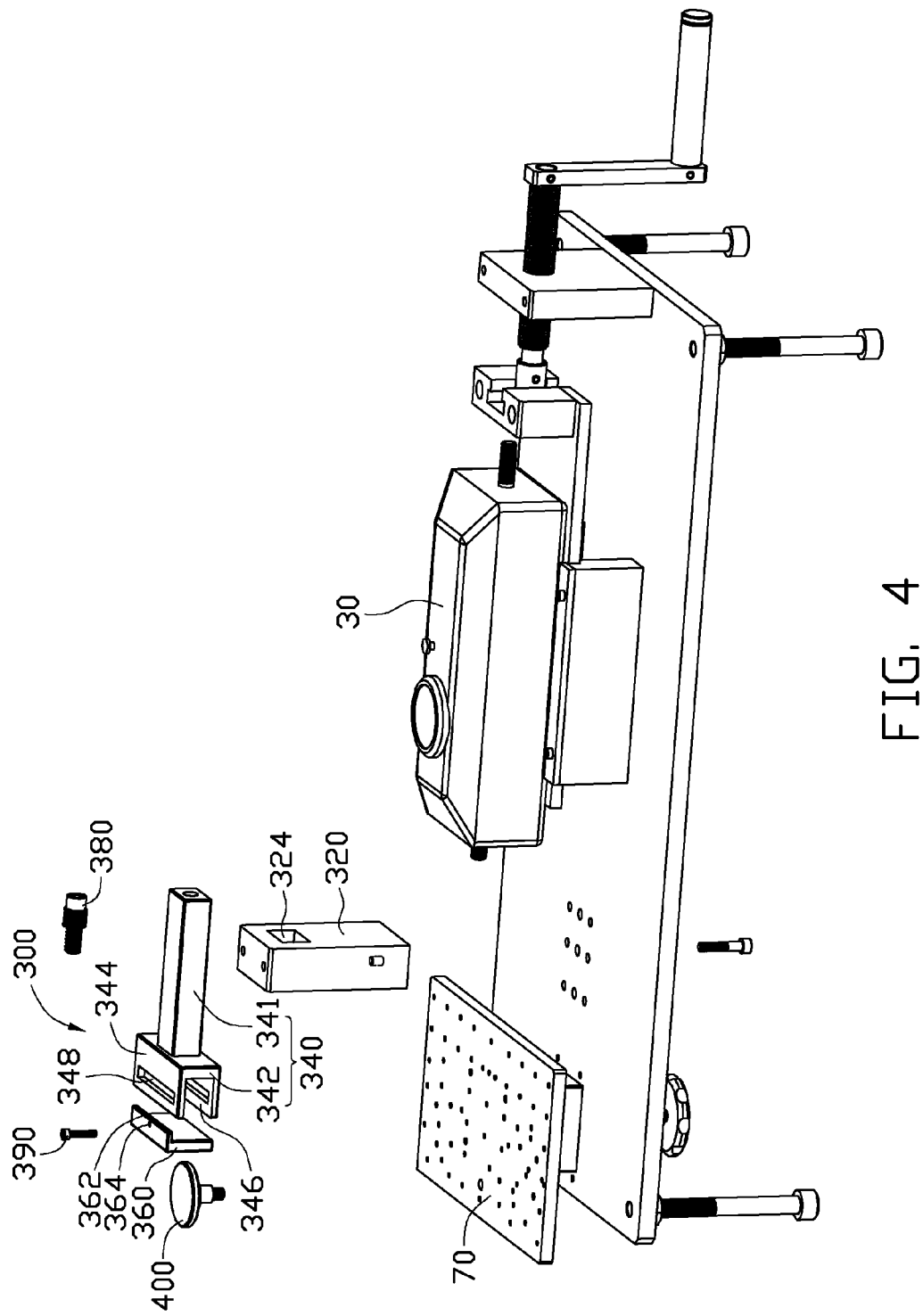
FIG. 4 is an exploded, isometric view showing another exemplary embodiment of an apparatus for testing object strength.

Referring to FIG. 4, a second exemplary embodiment of an apparatus for testing object strength is shown. The apparatus includes a push-pull mechanism 300 and a clamping mechanism 400, differing from those of the first exemplary embodiment only in that push-pull mechanism 300 includes a stand portion 320, a sliding portion 340, a driving portion 360, a connecting portion 380, and an adjusting element 390. A rectangular sliding channel 324 is defined through the top of the stand portion 320. The sliding portion 340 includes a rectangular sliding shaft 341 extending through the sliding channel 324, and a mounting section 342 extending from an end of the sliding shaft 341. The mounting section 342 includes two spaced mounting boards 344, one above another. A receiving space 346 is defined between the two mounting boards 344. Two aligning through slots 348 are defined through the two mounting boards 344, respectively. The driving portion 360 is a board which extends through the through slots 348 to be located between the two mounting boards 344. A mounting flange 362 defining a fixing hole 364 therein is formed from the top of the driving portion 360. The clamping mechanism 400 is a bulge-head bolt received in the installation board 70.

Figure 5:
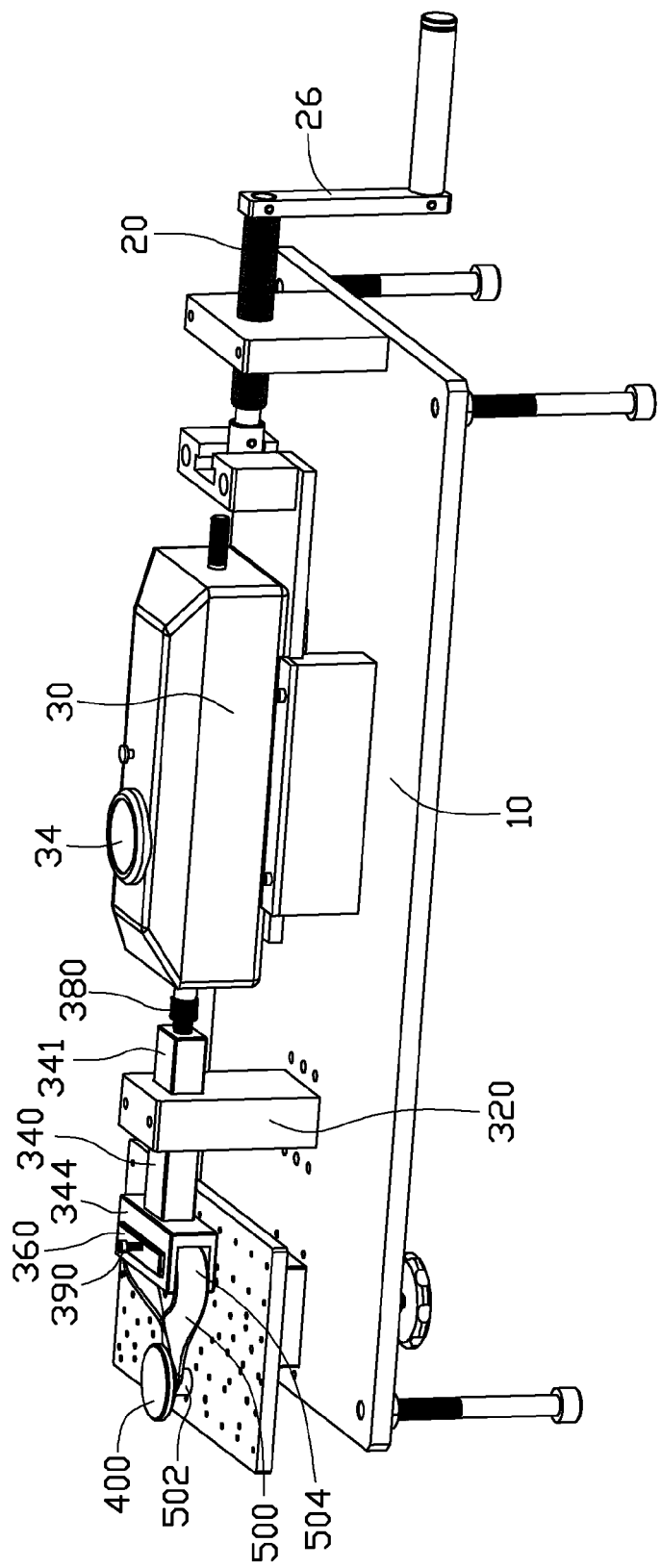
FIG. 5 is an assembled view of the apparatus of FIG. 4, during testing of another object.

Referring also to FIG. 5, in assembly, the stand portion 320 of the push-pull mechanism 300 is fixed on the platform 10 and located between the installation board 70 and the force gauge 30. The sliding shaft 341 slidably extends through the sliding channel 324. The connecting portion 380 connects the force gauge 30 to the sliding portion 340. The adjusting element 390 extends through the fixing hole 364 of the driving portion 360. The driving portion 360 extends through the through slots 348 of the mounting board 344 to make the distal end of the adjusting element 390 abut against the upper mounting board 344.

During strength testing of another product 500 including a pull tab 502 and a pull ring 504, the driving portion 360 is taken out from the through slots 348, the pull ring 504 is received in the receiving space 346 of the driving portion 340, and then the driving portion 360 is inserted through the through slots 348 of the mounting board 344 again. Thus, the driving portion 360 is blocked and received in the pull ring 504. The clamping mechanism 400 extends through the pull tab 502, and is received in the installation board 70. The handle 26 of the drive mechanism 20 is rotated to move the force gauge 30 away from the product 500. The clamping mechanism 400 exerts a force on the pull tab 502 opposite to that the driving portion 360 exerts on the pull ring 504. When the reading on the dial 34 of the force gauge 30 equals or exceeds a predetermined value, the handle 26 stops rotating. In this circumstance, if the pull tab 502 and the pull ring 504 do not rupture, the strength testing of the product 500 passes; if the pull tab 502 and the pull ring 504 rupture, the strength testing of the product 500 does not pass.

Thus, the push-pull mechanism 300 and the clamping mechanism 400 can be changed readily according to the situations of the product to be tested.

It is to be understood, however, that even though numerous characteristics and advantages of the disclosure have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. An apparatus for testing strength of a corner portion of an object, the apparatus comprising:
a support platform;
an installation mechanism comprising a slidable plate slidably mounted on the support platform;
a force gauge fixed to the slidable plate;
a drive mechanism connected to the slidable plate to move the slidable plate and the force gauge; and
a push-pull mechanism connected to the force gauge to be pushed or pulled by the force gauge and exerting push or pull force on the corner portion of the object; wherein the push-pull mechanism comprises a stand portion fixed on the platform, a sliding portion mounted to the stand portion and slidable relative to the stand portion, a driving portion attached to the sliding portion to exert force on two sides of the corner portion to urge the two sides to be deformed toward different directions, and a connecting portion connecting the force gauge and the sliding portion;
wherein the driving portion comprises a fixing flange extending out from a top thereof; the fixing flange defines a fixing hole; the push-pull mechanism further comprises an adjusting element received in the fixing hole of the fixing flange; and a distal end of the adjusting element abuts the sliding portion to adjust position of the driving portion relative to the sliding portion.

2. The apparatus of claim 1, wherein the stand portion comprises a sliding channel; the sliding portion comprises a sliding shaft slidably extending through the sliding channel, and a mounting section extending from an end of the sliding shaft; a through hole is defined through the mounting section from top to bottom for mounting the driving portion, and the adjusting element abuts the mounting section.

3. The apparatus of claim 2, wherein the mounting section defines a fastener hole in a distal end thereof and communicating with the through hole, a fastener extends through the fastener hole of the mounting section and abuts the driving portion to lock the driving portion relative to the mounting section.

4. The apparatus of claim 3, wherein the driving portion defines a notch in a side edge thereof, the fastener engages in the notch to lock the driving portion.

5. The apparatus of claim 2, wherein the driving portion comprises a rectangular main body extending through the through hole of the mounting section, the fixing flange extending out from the top of the main body, and a pair of forcing posts extending down from two diagonal corners of the bottom of the main body; two sidewalls of each forcing post are coplanar with two sidewalls of the corresponding corner of the main body, respectively.

6. The apparatus of claim 2, wherein the force gauge comprises a threaded fastener extending from an end thereof, the sliding shaft of the sliding portion defines a securing hole in an end thereof; the connecting portion comprises a threaded post at one end to engage in the securing hole of the sliding portion, and a threaded sleeve at the other end to receive the threaded fastener of the force gauge.

7. The apparatus of claim 2, further comprising an adjustment mechanism installed on the support platform, and an installation board fixed on the adjustment mechanism to support the object.

8. The apparatus of claim 7, further comprising a clamping mechanism to fix the object on the installation board.

9. An apparatus for testing object strength, the apparatus comprising:
   a support platform;
   an installation mechanism comprising a slidable plate slidably mounted on the support platform;
   a force gauge fixed to the slidable plate;
   a drive mechanism connected to the slidable plate to move the slidable plate and the force gauge; and
   a push-pull mechanism connected to the force gauge to be pushed or pulled by the force gauge and exerting push or pull force on the object; wherein the push-pull mechanism comprises a stand portion fixed on the platform, a sliding portion mounted to the stand portion and slidable relative to the stand portion, a driving portion attached to the sliding portion to exert force on the object, and a connecting portion connecting the force gauge and the driving portion;
   wherein the force gauge comprises a threaded fastener extending from an end thereof; the connecting portion comprises a threaded post at one end to engage in the sliding portion, and a threaded sleeve at the other end to receive the threaded fastener of the force gauge.

10. The apparatus of claim 9, wherein the sliding portion comprises a mounting section with two opposite mounting boards, in each of which a through slot is defined; wherein the driving portion is a board extending through the through slots to between the two mounting boards to exert force on the object.

11. The apparatus of claim 10, wherein the sliding portion further comprises a sliding shaft with a securing hole defined in an end thereof; the threaded post of the connecting portion is received in the securing hole of the sliding portion.

12. The apparatus of claim 10, further comprising an adjustment mechanism installed on the support platform, and an installation board fixed on the adjustment mechanism to support the object.

13. The apparatus of claim 12, further comprising a clamping mechanism, wherein the clamping mechanism is a bulge-head bolt received in the installation board to fix the object on the installation board and exerts force on the object together with the driving portion.

14. An apparatus for testing strength of a corner portion of an object, the apparatus comprising:
   a support platform;
   an installation mechanism comprising a slidable plate slidably mounted on the support platform;
   a force gauge fixed to the slidable plate;
   a drive mechanism connected to the slidable plate to move the slidable plate and the force gauge; and
   a push-pull mechanism connected to the force gauge to be pushed or pulled by the force gauge and exerting push or pull force on the corner portion of the object; wherein the push-pull mechanism comprises a stand portion fixed on the platform, a sliding portion mounted to the stand portion and slidable relative to the stand portion, a driving portion attached to the sliding portion to exert force on two sides of the corner portion to urge the two sides to be deformed toward different directions, and a connecting portion connecting the force gauge and the sliding portion;
   wherein the force gauge comprises a threaded fastener extending from an end thereof, the connecting portion comprises a threaded post at one end to engage in the sliding portion, and a threaded sleeve at the other end to receive the threaded fastener of the force gauge.

* * * * *